United States Patent
Bieri et al.

(10) Patent No.: US 12,084,460 B2
(45) Date of Patent: Sep. 10, 2024

(54) CRYSTALLINE FORMS OF A TLR7/TLR8 INHIBITOR

(71) Applicant: NOVARTIS AG, Basel (CH)

(72) Inventors: Nicole Bieri, Muttenz (CH); Andreas Kordikowski, Binningen (CH); Bin Li, Changshu (CN); Philipp Lustenberger, Allschwil (CH); Rita Ramos, Allschwil (CH); Vijay Sethuraman, Fremont, CA (US); Sisi Zhang, Changshu (CN)

(73) Assignee: Novartis AG, Basel (CH)

( * ) Notice: Subject to any disclaimer, the term of this patent is extended or adjusted under 35 U.S.C. 154(b) by 767 days.

(21) Appl. No.: 17/056,351

(22) PCT Filed: May 16, 2019

(86) PCT No.: PCT/IB2019/054066
§ 371 (c)(1),
(2) Date: Nov. 17, 2020

(87) PCT Pub. No.: WO2019/220390
PCT Pub. Date: Nov. 21, 2019

(65) Prior Publication Data
US 2021/0206783 A1    Jul. 8, 2021

(30) Foreign Application Priority Data

May 18, 2018   (WO) ............... PCT/CN2018/087448

(51) Int. Cl.
*A61K 31/4162*   (2006.01)
*A61K 31/5377*   (2006.01)
(Continued)

(52) U.S. Cl.
CPC ........ *C07D 519/00* (2013.01); *A61K 31/4162* (2013.01); *A61K 31/5377* (2013.01);
(Continued)

(58) Field of Classification Search
CPC .. C07D 413/14; C07D 519/00; C07D 487/04; C07D 265/30; C07D 231/00;
(Continued)

(56) References Cited

U.S. PATENT DOCUMENTS

| 6,103,728 | A  | 8/2000 | Tang et al. |
| 2019/0177325 | A1 | 6/2019 | Wang et al. |

FOREIGN PATENT DOCUMENTS

| WO | 2007022280 A1 | 2/2007 |
| WO | 2012/097000 | 7/2012 |

(Continued)

OTHER PUBLICATIONS

Hirayama, Yukikagoutbutsu Kessyo Sakusei Handbook (Handbook of Organic Compound Crystal Preparation), 2008, 17-23, 37-40, 45-51, 57-65.
Reichard et al, Solvents and environmental effects in organic chemistry, Mir Publishing House, 1991, 611-614, 763.
International Search and Written Opinion for International Application No. PCT/IB2019/054066, mailed Aug. 7, 2019 (13 pages).
Caira, "Crystalline Polymorphism of Organic Compounds," Topics in Current Chemistry. 198:163-208 (1998).
(Continued)

*Primary Examiner* — Craig D Ricci
*Assistant Examiner* — Janet L Coppins
(74) *Attorney, Agent, or Firm* — Francine F. Li

(57) ABSTRACT

This application relates to various crystalline forms of (S)—N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)morpholine-3-carboxamide in its free form, as well as compositions, method of making and methods of using the same. In some embodiments the crystalline forms also contain water ("hydrates"). These materials are useful in the treatment of various autoimmune diseases, including systemic lupus erythematosus, cutaneous lupus, discoid lupus, mixed connective tissue disease, primary biliary cirrhosis, immune thrombocytopenia purpura, hidradenitis suppurativa, dermatomyositis, polymyositis, Sjögren's syndrome, arthritis, rheumatoid arthritis and psoriasis.

15 Claims, 6 Drawing Sheets

(51) Int. Cl.
*A61K 45/06* (2006.01)
*C07D 231/00* (2006.01)
*C07D 519/00* (2006.01)
*A61K 31/437* (2006.01)
*C07D 265/30* (2006.01)
*C07D 487/04* (2006.01)

(52) U.S. Cl.
CPC ............ *A61K 45/06* (2013.01); *C07D 231/00* (2013.01); *A61K 31/437* (2013.01); *C07B 2200/13* (2013.01); *C07D 265/30* (2013.01); *C07D 487/04* (2013.01)

(58) Field of Classification Search
CPC ............ A61K 31/4188; A61K 31/5377; A61K 31/437; A61K 31/4162
See application file for complete search history.

(56) References Cited

FOREIGN PATENT DOCUMENTS

| WO | 2013117615 A1 | 8/2013 | | |
|---|---|---|---|---|
| WO | 2015/017460 A1 | 2/2015 | | |
| WO | WO-2018047081 A1 * | 3/2018 | ............ | A61K 31/437 |

OTHER PUBLICATIONS

Rodriguez-Spong et al., "General Principles of Pharmaceutical Solid Polymorphism: a Supramolecular Perspective", Advanced Drug Reviews, vol. 56, pp. 241-274, (2004).
Reichard et al., "Solvents and environmental effects in organic chemistry", Mir Publishing House, vol. 763 (pp. 611-614, (1991).
Caira, Mino R., "Crystalline Polymorphism of Organic Compounds", Topics in Current Chemistry, vol. 198, pp. 163-208, (1998).

* cited by examiner

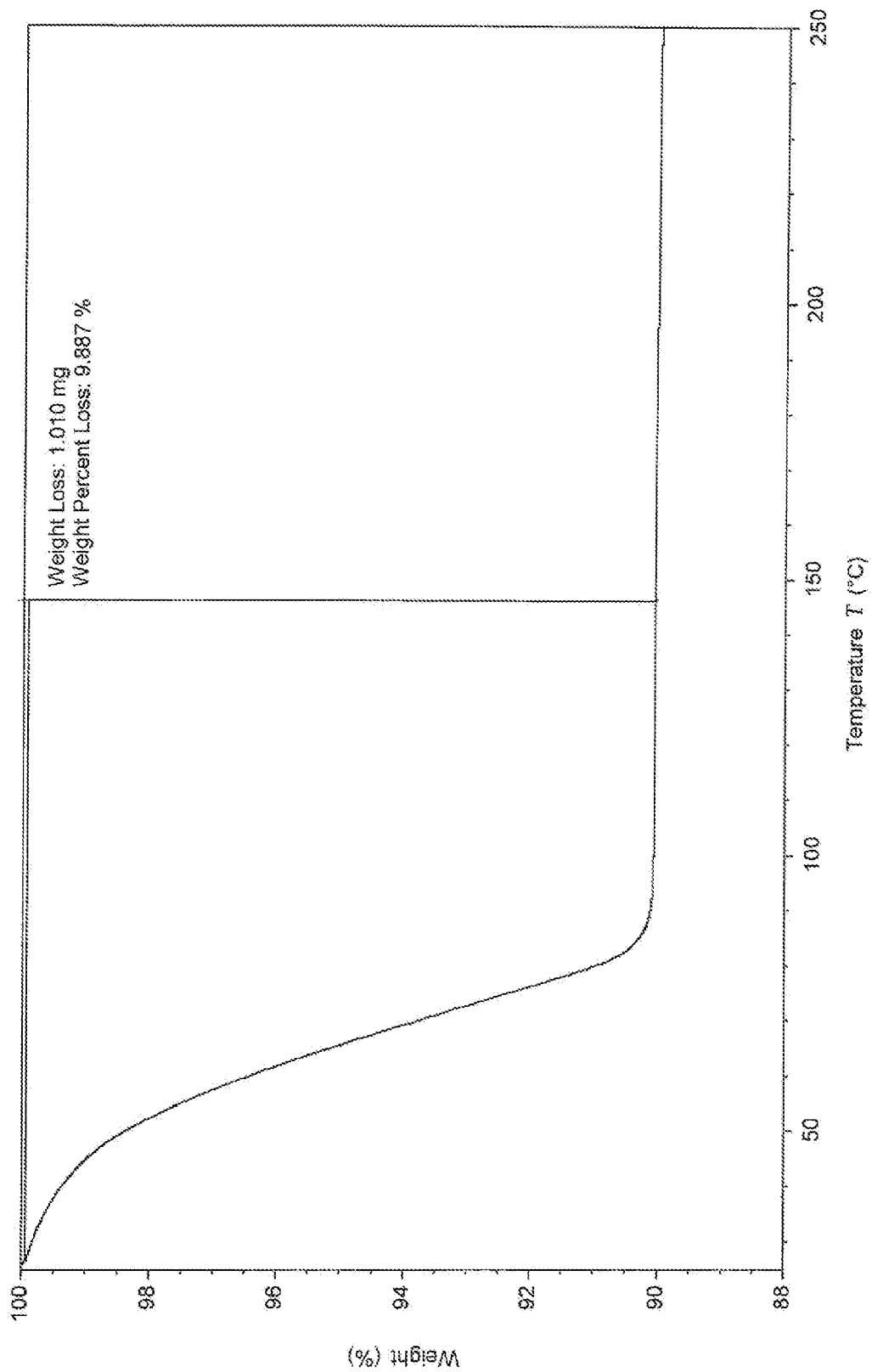

CRYSTALLINE FORMS OF A TLR7/TLR8 INHIBITOR

FIELD OF INVENTION

The present disclosure generally relates to crystalline forms of (S)—N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)morpholine-3-carboxamide. The present disclosure also generally relates to a pharmaceutical composition comprising the crystalline forms, as well of methods of making and methods of using the crystalline forms in the treatment of particular autoimmune diseases associated with the activity of an endosomal Toll-like Receptor selected from TLR7 and TLR8, and methods for obtaining such crystalline forms.

BACKGROUND (S)—N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)morpholine-3-carboxamide was first disclosed as an HCl salt in WO2018/047081, filed Sep. 6, 2017, which is incorporated by reference in its entirety, and is a dual inhibitor of TLR7 and TLR8 having the structure of Formula I:

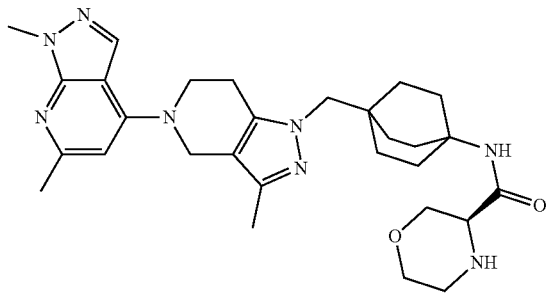

Formula I

The compound of Formula I is useful in the treatment of various autoimmune disease states associated with the activity of an endosomal Toll-like Receptor selected from TLR7 and TLR8. As such, the compound of Formula I is therefore useful in the treatment of certain autoimmune diseases, including, for example, systemic lupus erythematosus, cutaneous lupus, discoid lupus, mixed connective tissue disease, primary biliary cirrhosis, immune thrombocytopenia purpura, hidradenitis suppurativa, dermatomyositis, polymyositis, Sjögren's syndrome, arthritis, rheumatoid arthritis or psoriasis.

Solid state form of the active pharmaceutical ingredient (API) of a particular drug is often an important determinant of the drug's ease of preparation, hygroscopicity, stability, solubility, storage stability, ease of formulation, rate of dissolution in gastrointestinal fluids and in vivo bioavailability. Crystalline forms occur where the same composition of matter crystallizes in a different lattice arrangement resulting in different thermodynamic properties and stabilities specific to the particular crystalline form. Crystalline forms may also include different hydrates or solvates of the same compound. In deciding which form is preferable, the numerous properties of the forms are compared and the preferred form chosen based on the many physical property variables. It is entirely possible that one form can be preferable in some circumstances where certain aspects such as ease of preparation, stability, etc. are deemed to be critical. In other situations, a different form may be preferred for greater dissolution rate and/or superior bioavailability. It is not yet possible to predict whether a particular compound or salt of a compound will form polymorphs, whether any such polymorphs will be suitable for commercial use in a therapeutic composition, or which polymorphs will display such desirable properties.

SUMMARY

The present disclosure provides crystalline forms of (S)—N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)morpholine-3-carboxamide in a free form (i.e. a non-salt form). In a particular embodiment, the free form further includes water (referred to herein as hydrate).

The present disclosure therefore provides a crystalline form of (S)—N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)morpholine-3-carboxamide in a free form.

The present disclosure further provides a crystalline form of a hydrate of (S)—N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)morpholine-3-carboxamide. Embodiments of these crystalline forms include those forms designated herein as Form A and Form $H_A$. The names used herein to identify a specific form, e.g. "Form A" or "Form $H_A$", should not be considered limiting with respect to any other substance possessing similar or identical physical and chemical characteristics, but rather it should be understood that these designations are mere identifiers that should be interpreted according to the characterization information also presented herein.

BRIEF DESCRIPTION OF THE DRAWINGS

FIG. 6 provides an illustrative TGA for a hydrate form of the compound of Formula I, designated herein as Form $H_A$.

Figure 1:
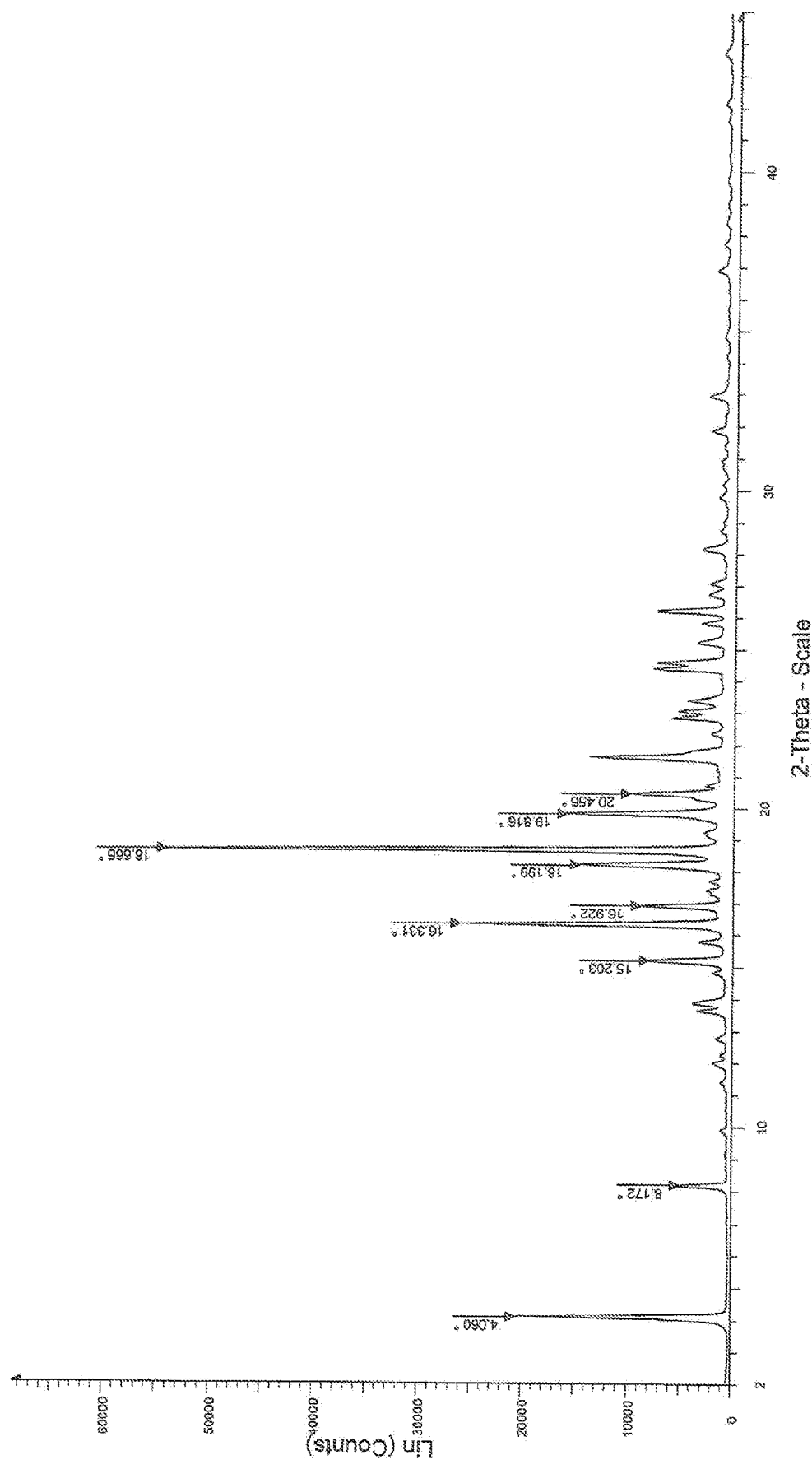
FIG. 1 provides an illustrative XRPD spectrum for the free form of compound of Formula I, designated herein as Form A, showing degrees 2θ (2-theta) on the X-axis and relative intensity on the Y-axis.

More detailed listings of the XRPD peaks for each of forms A and $H_A$ are set forth in Tables 1 and 2, respectively below, in which the % relative intensity ($I/I_0 \times 100$) is also provided. It should be understood that in the X-ray powder diffraction spectra or pattern that there is inherent variability in the values measured in degrees 2θ (°2θ) as a result of, for example, instrumental variation (including differences between instruments). As such, it should be understood that there is a variability of up to ±0.2°2θ in XRPD peak measurements and yet such peak values would still be considered to be representative of a particular solid state form of the crystalline materials described herein. It should also be understood that other measured values from XRPD experiments and DSC/TGA experiments, such as relative intensity and water content, can vary as a result of, for example, sample preparation and/or storage and/or environmental conditions, and yet the measured values will still be considered to be representative of a particular solid state form of the crystalline materials described herein.

DETAILED DESCRIPTION OF THE DISCLOSURE

The present disclosure relates to a crystalline form of the free form of (S)—N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)morpholine-3-carboxamide (the compound of Formula I), which is described and characterized herein.

The present invention also relates to a crystalline form of a hydrate of (S)—N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)morpholine-3-carboxamide. More specifically, the present invention relates to a crystalline form a hemiheptahydrate of (S)—N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)morpholine-3-carboxamide, which is described and characterized herein.

In one embodiment, the present disclosure provides a crystalline form of the free form of (S)—N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)morpholine-3-carboxamide (Form A) having an X-ray powder diffraction (XRPD) pattern comprising a representative peak, in terms of °2θ, at 18.6±0.2°2θ measured at a temperature of about 25° C. In another embodiment, the XRPD pattern further comprises one or more additional representative peaks chosen from 4.1±0.2°2θ and 16.3±0.2°2θ. In one aspect of the previous embodiment, the XRPD pattern further comprises one or more additional representative peaks chosen from 18.2±0.2°2θ, and 19.8±0.2°2θ measured at a temperature of about 25° C. Accordingly, the XRPD pattern for the crystalline form of the free form of the compound of Formula I may comprise one, two, three, or four representative peaks selected from 18.6±0.2°2θ, 4.1±0.2°2θ, 16.3±0.2°2θ, 18.2±0.2°2θ, and 19.8±0.2°2θ measured at a temperature of about 25° C. In another embodiment, the crystalline form of the free form of the compound of Formula I has an XRPD pattern that may further include one or more additional representative peaks chosen from 8.2±0.2°2θ, 15.2±0.2°2θ and 16.9±0.2°2θ measured at a temperature of about 25° C. Thus, the XRPD pattern for the crystalline form of the free form of the compound of Formula I may comprise one, two, three, four, five or six representative peaks selected from 18.6±0.2°2θ, 4.1±0.2°2θ, 16.3±0.2°2θ, 18.2±0.2°2θ, 19.8±0.2°2θ, 8.2±0.2°2θ, 15.2±0.2°2θ and 16.9±0.2°2θ measured at a temperature of about 25° C. The XRPD pattern for the crystalline form of the free form of the compound of Formula I may comprise one, two, three, four, five or six representative peaks selected from the peaks disclosed in table 1 and measured at a temperature of about 25° C.

In another aspect of the above embodiment, the crystalline form of the free form of compound of Formula I is characterized by a x-ray powder diffraction pattern comprising four or more 2θ values (CuKα λ=1.54184 Å) selected from the group consisting of 4.1±0.2°, 8.2±0.2°, 15.2±0.2°, 16.3±0.2°, 16.9±0.2°, 18.2±0.2°, 18.6±0.2°, 19.8±0.2° and 20.4±0.2, measured at a temperature of about 25° C.

In another aspect of the above embodiment, the crystalline form of the free form of compound of Formula I is characterized by a x-ray powder diffraction pattern comprising five or more 2θ values (CuKα λ=1.54184 Å) selected from the group consisting of 4.1±0.2°, 8.2±0.2°, 15.2±0.2°, 16.3±0.2°, 16.9±0.2°, 18.2±0.2°, 18.6±0.2°, 19.8±0.2° and 20.4±0.2, measured at a temperature of about 25° C.

In yet another aspect of the above embodiment, the crystalline form of the free form of the compound of Formula I has an XRPD pattern substantially as shown in FIG. 1. It should be understood that the water content of Form A can be in the range of about 0% to about 1.5% and still be considered to be a crystalline form having the XRPD pattern comprising the one, two, three, four, five or six representative peaks described above or in table 1. The water content as determined by Karl Fischer titration method for Form A is 0.9%.

The crystalline form of the free form of (S)—N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)morpholine-3-carboxamide may be characterized thermally. In one embodiment, a crystalline form of the free form of the compound of Formula I has a thermal profile measured by Differential Scanning Calorimetry (DSC) with a heating rate of 10° C./min comprising a single endothermic peak starting at about 182.7° C. with enthalpy ΔH of 65 J/g.

Figure 2:
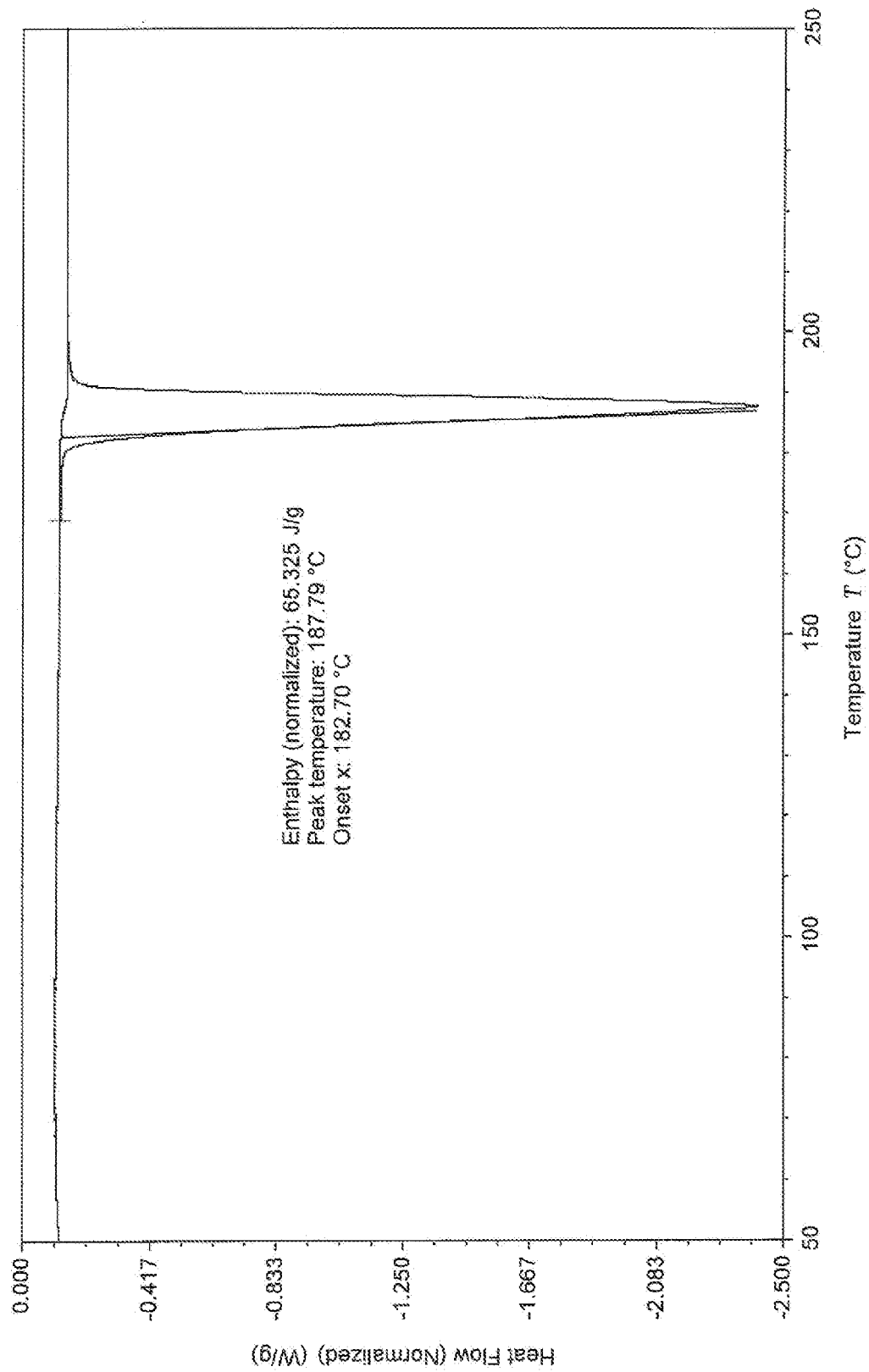
FIG. 2 provides an illustrative DSC for the free form of the compound of Formula I, designated herein as Form A.

In another embodiment, the crystalline form of the free form of the compound of Formula I has a DSC thermogram that is substantially as shown in FIG. 2. It should be understood that hydrated forms may yield different thermograms (in terms of peak shape and profile) depending on instrument parameters, thus the same material may have thermograms that look substantially different from each other when the data is generated on two different instruments.

Figure 3:
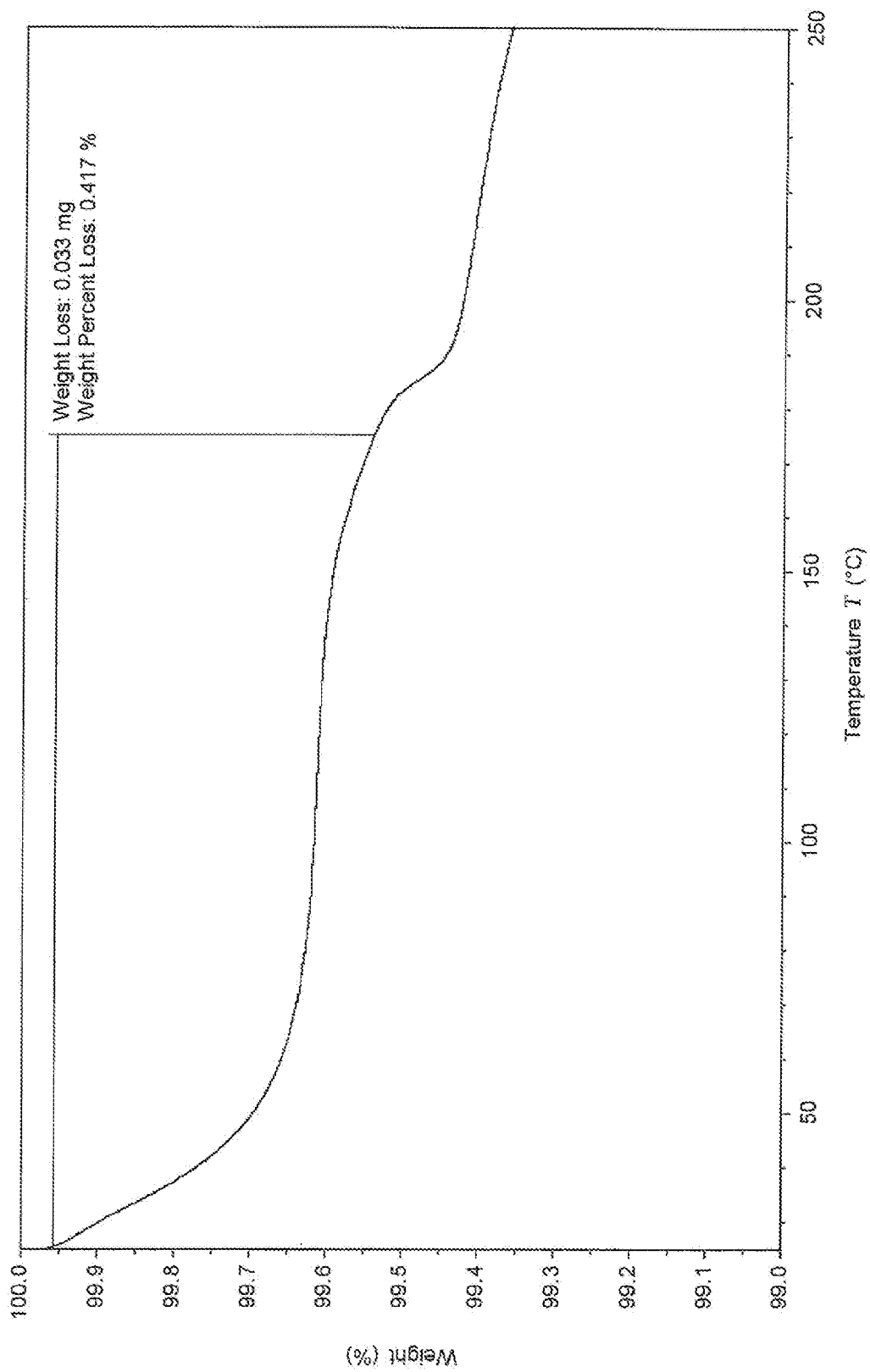
FIG. 3 provides an illustrative TGA for the free form of the compound of Formula I, designated herein as Form A.

In another embodiment, the crystalline form of the free form of the compound of Formula I has a thermogravimetric analysis (TGA) diagram substantially the same as that shown in shown in FIG. 3. The weight loss by TGA is about 0.4% at 182° C.

In yet another embodiment, the crystalline form A is substantially phase pure.

In yet another embodiment, the invention pertains to a process for making crystalline Form A of compound (S)—N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)morpholine-3-carboxamide, said method comprises the steps of:
  a) Suspending an amorphous free form of (S)—N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)morpholine-3-carboxamide in acetone or isopropanol to form a suspension mixture,
  b) Heating the suspension mixture to a temperature of about 50° C. until dissolution to form a solution,
  c) Cooling the solution to about 15° C. over a period of about 4 h to form a suspension mixture,
  d) Optionally repeating the steps b) and c) once or twice,
  e) Heating the suspension mixture to about 50° C. and adding heptane dropwise, f) Stirring the mixture at 50° C. for about 1 h, g) Cooling the solution to about 15° C. over a period of about 4 h to form a suspension mixture,
h) Stirring the suspension mixture at 15° C. for 1 h, and
i) Filtering the suspension to collect the crystalline Form A.

The present invention further provides a crystalline form of a hydrate of (S)—N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)morpholine-3-carboxamide (Form $H_A$) having an X-ray powder diffraction (XRPD) pattern comprising a representative peak, in terms of °2θ, at 14.3±0.2°2θ, measured at a temperature of about 25° C. In another embodiment, the XRPD pattern further comprises one or more additional representative peaks chosen from 6.6±0.2°2θ, 16.0±0.2°2θ, and 17.3±0.2°2θ, measured at a temperature of about 25° C. Alternatively, the XRPD pattern for the crystalline form of said hydrate of the compound of Formula I may comprise one, two, three, or four representative peaks chosen from 14.3±0.2°2θ, 6.6±0.2°2θ, 16.0±0.2°2θ, and 17.3±0.2°2θ, measured at a temperature of about 25° C.

In another embodiment, the crystalline form of said hydrate of the compound of Formula I has an XRPD pattern that may further include one or more additional representative peaks chosen from 23.5±0.2°2θ, 26.5±0.2°2θ, 27.3±0.2°2θ. Thus, the XRPD pattern for the crystalline form of said hydrate of the compound of Formula I may comprise one, two, three, four, five or six representative peaks chosen from 14.3±0.2°2θ, 6.6±0.2°2θ, 16.0±0.2°2θ, 17.3±0.2°2θ, 23.5±0.2°2θ, 26.5±0.2°2θ and 27.3±0.2°2θ or chosen from peaks disclosed in table 2 and measured at a temperature of about 25° C.

In another embodiment, said hydrate form is characterized by a x-ray powder diffraction pattern comprising four or more 2θ values (CuKα λ=1.54184 Å) selected from the group consisting of 6.6±0.2°, 7.1±0.2°, 10.6±0.2°, 13.2±0.2°, 14.3±0.2°, 16.0±0.2°, 17.3±0.2°, 23.5±0.2°, 26.5±0.2 and 27.3±0.2°2θ, measured at a temperature of about 25° C.

In another embodiment, said hydrate form is characterized by a x-ray powder diffraction pattern comprising five or more 2θ values (CuKα λ=1.54184 Å) selected from the group consisting of 6.6±0.2°, 7.1±0.2°, 10.6±0.2°, 13.2±0.2°, 14.3±0.2°, 16.0±0.2°, 17.3±0.2°, 23.5±0.2°, 26.5±0.2 and 27.3±0.2°2θ, measured at a temperature of about 25° C.

Figure 4:
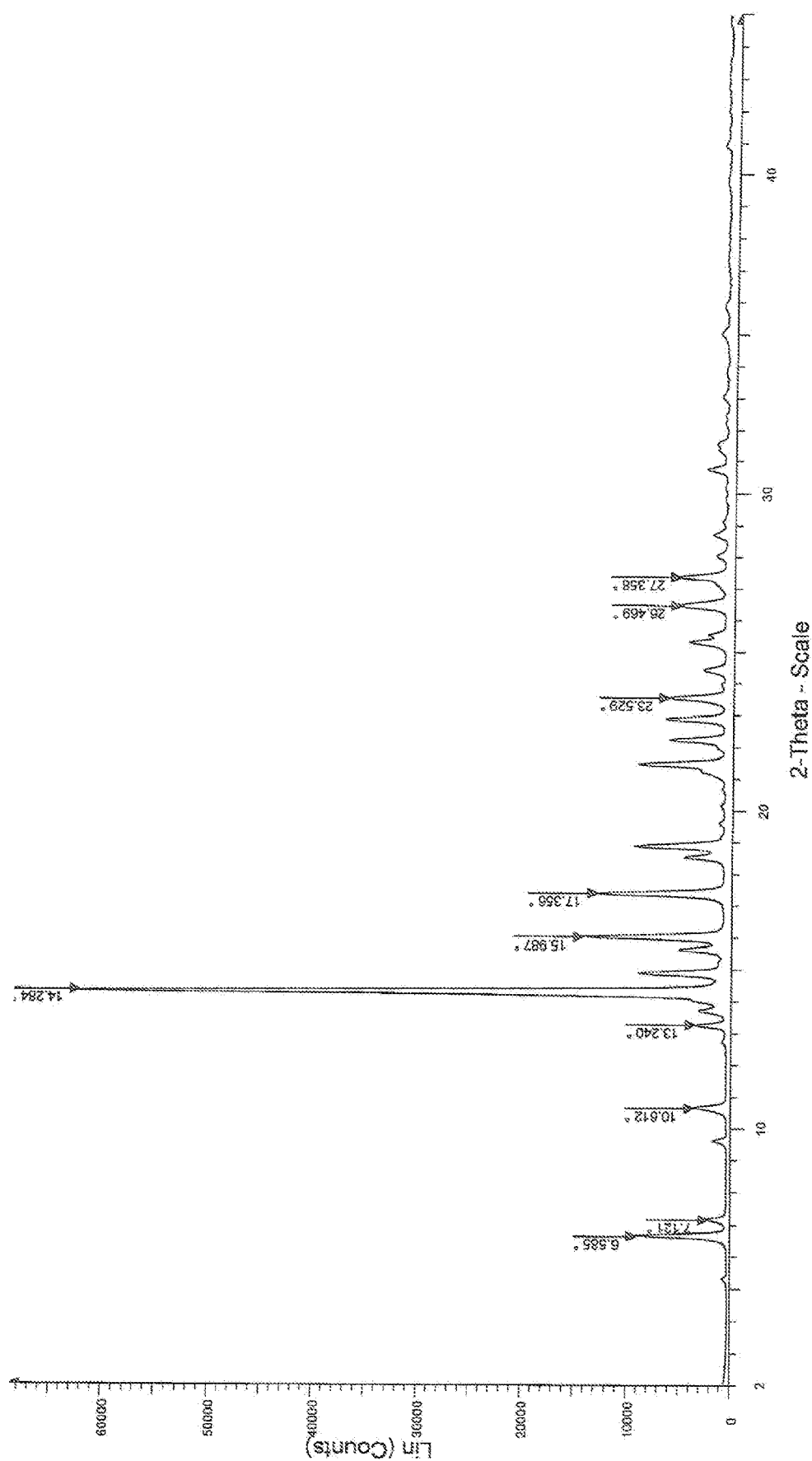
FIG. 4 provides an illustrative XRPD spectrum for a hydrate form of the compound of Formula I, designated herein as Form $H_A$, showing degrees 2θ (2-theta) on the X-axis and relative intensity on the Y-axis.

In yet another embodiment, a crystalline form of a hydrate of the compound of Formula I has an XRPD pattern substantially as shown in FIG. 4. It should be understood that the water content of Form $H_A$ can be in the range of about 9% to about 12% and still be considered to be a hydrate having the XRPD pattern comprising the one, two, three, four, five or six representative peaks described above. The water content as determined by Karl Fischer titration method for Form $H_A$ is 10.6%.

The crystalline form of the hydrate of (S)—N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)morpholine-3-carboxamide may be characterized thermally. In one embodiment, a crystalline form of the hydrate of the compound of Formula I has a differential thermogravimetric profile comprising an endothermic peak starting at about 54.2° C. with an enthalpy ΔH of 284 J/g (corresponding to the dehydration) and an endothermic peak starting at about 130.6° C. with an enthalpy ΔH of 24 J/g (corresponding to the melting).

Figure 5:
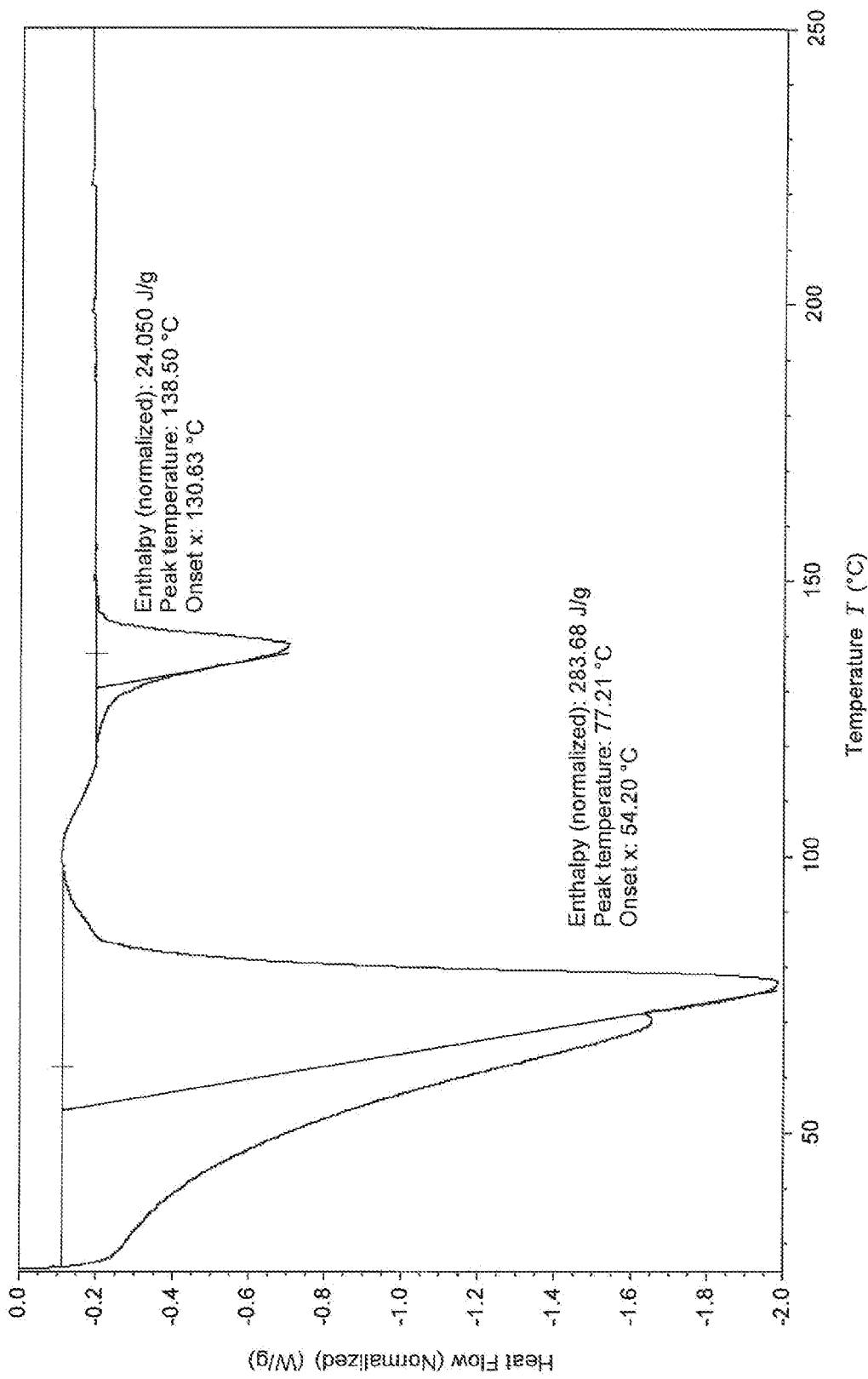
FIG. 5 provides an illustrative DSC for a hydrate form of the compound of Formula I, designated herein as Form $H_A$.

In another embodiment, a crystalline form of the hydrate of the compound of Formula I has a DSC thermogram that is substantially as shown in FIG. 5. It should be understood that hydrated forms may yield different thermograms (in terms of peak shape and profile) depending on instrument parameters, thus the same material may have thermograms that look substantially different from each other when the data is generated on two different instruments.

In another embodiment, a crystalline form of the hydrate of the compound of Formula I has a thermo gravimetric analysis (TGA) diagram substantially the same as that shown in shown in FIG. 6. The weight loss by TGA is about 9.9% at 96° C.

In yet another embodiment, the crystalline form $H_A$ described above is a hemiheptahydrate form.

In yet another embodiment, the crystalline form $H_A$ is substantially phase pure.

In yet another embodiment, the invention pertains to a process for making crystalline Form $H_A$ of compound (S)—N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)morpholine-3-carboxamide, said method comprises the steps of:
a) Suspending an amorphous free form of (S)—N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)morpholine-3-carboxamide in a solvent mixture containing at least about 2% by weight of water to form a suspension mixture,
b) Heating the suspension mixture to a temperature until dissolution to form a solution,
c) Cooling the solution to about −10° C. to form a suspension,
d) Filtering the suspension to collect the crystalline Form $H_A$.

In a particular aspect of the above embodiment, the invention pertains to a process for making crystalline form A wherein the solvent mixture in step a) comprises acetone, alcohol, tetrahydrofuran or acetonitrile.

In yet another aspect of the previous embodiment, the invention pertains to a process of making crystalline form A wherein the solvent mixture in step a) is selected from acetone/water 98:2 (weight by weight) and isopropanol/water 95:5 (weight by weight).

In another embodiment, the invention relates to a pharmaceutical composition comprising a therapeutically effective amount of a crystalline form of (S)—N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)morpholine-3-carboxamide (Form A or Form $H_A$ or a combination thereof), and at least one pharmaceutically acceptable carrier, diluent or excipient. In a particular embodiment, the invention relates to a pharmaceutical composition comprising crystalline form A, and one or more pharmaceutically acceptable carriers, diluents or excipients. In yet another aspect, the invention relates to a pharmaceutical composition comprising crystalline form A in substantially pure phase. In yet another embodiment, the invention relates to a pharmaceutical formulation comprising crystalline form A and further comprising at least one other solid state form of 5(S)—N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)morpholine-3-carboxamide. In one aspect of this embodiment, the other solid state form is crystalline form $H_A$. In yet another embodiment, the other solid state form is an amorphous form of (S)—N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)morpholine-3-carboxamide.

In a particular embodiment, the invention relates to a pharmaceutical composition comprising crystalline form $H_A$, and one or more pharmaceutically acceptable carriers, diluents or excipients. In yet another aspect, the invention relates to a pharmaceutical composition comprising crystalline form $H_A$ in substantially pure phase. In yet another embodiment, the invention relates to a pharmaceutical composition comprising crystalline form $H_A$ and further comprising at least one other solid state form of 5(S)—N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)morpholine-3-carboxamide. In one aspect of this embodiment, the other solid state form is crystalline form A. In yet another embodiment, the other solid state form is an amorphous form of (S)—N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)morpholine-3-carboxamide.

In other embodiments, the invention relates to combinations, in particular pharmaceutical combinations, comprising a therapeutically effective amount of a crystalline form of (S)—N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)morpholine-3-carboxamide (Form A, Form $H_A$ or combination thereof), and one or more therapeutic agents.

In a particular embodiment, the invention relates to a pharmaceutical combination comprising crystalline form A, and one or more therapeutic agents. In yet another aspect, the invention relates to a pharmaceutical combination comprising crystalline form A in substantially pure phase and one or more therapeutic agent. In yet another embodiment, the invention relates to a pharmaceutical combination comprising crystalline form A and further comprising at least one other solid state form of 5(S)—N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)morpholine-3-carboxamide. In one aspect of this embodiment, the other solid state form is crystalline form $H_A$. In yet another embodiment, the other solid state form is an amorphous form of (S)—N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)morpholine-3-carboxamide.

In a particular embodiment, the invention relates to a pharmaceutical combination comprising crystalline form $H_A$, and one or more therapeutic agents. In yet another aspect, the invention relates to a pharmaceutical combination comprising crystalline form $H_A$ in substantially pure phase and one or more therapeutic agent. In yet another embodiment, the invention relates to a pharmaceutical combination comprising crystalline form $H_A$ and further comprising at least one other solid state form of 5(S)—N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)morpholine-3-carboxamide. In one aspect of this embodiment, the other solid state form is crystalline form A. In yet another embodiment, the other solid state form is an amorphous form of (S)—N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)morpholine-3-carboxamide.

In another embodiment, the invention provides pharmaceutical combinations as described above wherein the second agent is independently selected from the group consisting of anti-inflammatory agents, immunomodulatory agents, immunosuppressive agents, cytokines, nonsteroidal anti-inflammatory drugs (NSAIDs), antimalarial compounds, anti-rheumatic compounds, inhibitors of B-cell activating factor (BAFF), inhibitors of B-lymphocyte stimulator (BLyS), and steroid hormones.

In one embodiment, the invention relates to a method of treating an autoimmune disease, in a subject in need thereof, the method comprising: administering to a subject in need thereof, a therapeutically effective amount of a crystalline form of (S)—N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)morpholine-3-carboxamide (Form A, Form $H_A$ or a combination thereof), alone or in combination with one or more therapeutic agents.

In another embodiment, the invention relates to a method of treating an autoimmune disease, in a subject in need thereof, comprising administering to said subject, a pharmaceutical composition as described above, alone or in combination with one or more therapeutic agents.

In another embodiment, the invention relates to a method of treating an autoimmune disease, in a subject in need thereof, comprising administering to said subject a pharmaceutical combination as described above.

In one embodiment, the invention relates to the use of a crystalline form of (S)—N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)morpholine-3-carboxamide (Form A, Form $H_A$ or a combination thereof), alone or in combination with one or more therapeutic agents, for the treatment of an autoimmune disease.

In yet another embodiment, the invention pertains to a crystalline form of (S)—N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)morpholine-3-carboxamide (Form A, Form $H_A$ or a combination thereof), for use in the treatment of an autoimmune disease.

In yet embodiment, the invention pertains to a combination of a crystalline form of (S)—N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)morpholine-3-carboxamide (Form A, Form $H_A$ or a combination thereof), and one or more therapeutic agents, for use in the treatment of an autoimmune disease.

In one embodiment, the invention relates to a method of treatment, a use, a compound for use, or a combination for use as described above, wherein the autoimmune disease is associated with the activity of an endosomal Toll-like Receptor selected from TLR7 and TLR8. In one aspect of this embodiment, the autoimmune disease associated with the activity of an endosomal Toll-like Receptor selected from TLR7 and TLR8 is selected from systemic lupus erythematosus, cutaneous lupus, discoid lupus, mixed connective tissue disease, primary biliary cirrhosis, immune thrombocytopenia purpura, hidradenitis suppurativa, dermatomyositis, polymyositis, Sjögren's syndrome, arthritis, rheumatoid arthritis and psoriasis.

In one embodiment, the invention relates to the method, the use or the combination for use according to the above embodiment, wherein therapeutic agent is administered together in a single composition or administered separately in two or more different compositions forms.

In one embodiment, the invention pertains to the method, the use or the combination for use as described above wherein the therapeutic agent is administered concurrently with, prior to, or subsequent to, a crystalline form of (S)—N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)morpholine-3-carboxamide.

The crystalline forms described herein have been found to have advantageous properties. The criteria for selection are toxicological considerations, crystallinity, melting point, hygroscopicity, stability in bulk, compatibility with excipients, pH of aqueous solution, solubility in water and aqueous media, morphology, handling and polymorphic behavior. Free form A and hydrate form $H_A$ have demonstrated superior behaviors, especially over the HCl salt which was previously known and described in WO2018/047081. The HCl salt was found to be deliquescent above 70% RH and also had a potential corrosivity.

Crystalline form A is an anhydrous form of (S)—N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)morpholine-3-carboxamide that is highly crystalline consisting of thin tabular particles. It is slightly hygroscopic up to 70% RH, picking up 1.3% of moisture, however, at higher humidities (i.e. above 70% RH), it transforms into the hydrate crystalline form $H_A$.

Crystalline form $H_A$ is a hydrated form of (S)—N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)morpholine-3-carboxamide. TGA and DVS data indicate that it is a hemiheptahydrate. Crystalline form $H_A$ is slightly hygroscopic at humidities above 30% RH. Below 20% RH, it dehydrates to a non-characterized anhydrate form that rehydrates back to the hydrate form $H_A$ once the humidity reaches 30% RH.

Stability in Solvent:

Competitive equilibrations were carried out to investigate the relative stability of form A and $H_A$ in a competitive solvent equilibration. A 1:1 mixture of form A and form $H_A$ was prepared and suspended in various solvents or mixture thereof at temperature between 25° C. and 50° C. for seven days. The resulting suspension was filtered and analyzed by XRPD/DVS. Competitive equilibration and the resulting data indicated that transformation of form A into form $H_A$ occurs at low water content. Results showed that transformation of form A into form $H_A$ occurs approximately at a water activity of $a_w$=0.25.

Solid State Stability in Bulk and with Excipient Mixtures

A stability and excipient compatibility study was performed on form A and form $H_A$. Both forms were subject to various test conditions as described below:

Test conditions in bulk: 1 week in a tight container at 80° C., 50° C., 80° C.-75% RH or 50° C.-75% RH.

Test condition with excipient mixtures (EM)
a. 1% of form A or form $H_A$ in EM1 for 2 weeks at 50° C.
b. 1% of form A or form $H_A$ in EM2 for 2 weeks at 50° C.
c. 10% of form A or form $H_A$ in crushed hard gelatin capsule (HGC) for 2 weeks at 50° C.
d. 10% of form A or form $H_A$ in crushed Hydroxypropyl Methyl Cellulose (HMPC) for 2 weeks at 50° C.
e. 1% of form A or form $H_A$ in EM1 for 2 weeks at 50° C. and 75% RH
f. 1% of form A or form $H_A$ in EM2 for 2 weeks at 50° C. and 75% RH
g. 10% of form A or form $H_A$ in crushed HGC for 2 weeks at 50° C. and 75% RH
h. 10% of form A or form $H_A$ in crushed HMPC for 2 weeks at 50° C. and 75% RH EM1: Excipient mixture 1: Lactose spray dried (53%), Microcrystalline Cellulose (MCC) PH102 (40%), Crospovidone XL (5%), Aerosil (0.5%), Magnesium stearate (1.5%)

EM2: Excipient mixture 2: Mannitol DC (68%), MCC PH102 (26%), Ac-Di-Sol (4%), Aerosil (0.5%), Magnesium stearate (1.5%)

The degradation products were analyzed by HPLC and the sample was analyzed by XPRD to detect any changes to the solid state.

Under the above described test conditions, both form A and form $H_A$ displayed good stability in bulk state and with excipients.

Additionally, both form A and form $H_A$ exhibit good physical and chemical stability under light exposure (exposure to 1200 kLux at 25° C.)

Physical Stability

Behavior under compression: The physical stability of each crystalline form (Form A or Form $H_A$) was also evaluated.

100 mg of the crystalline form was compressed for 5 minutes at 10 tons with a hydraulic press (diameter of the tablets 8 mm). The sample was then characterized by XRPD to detect any change in the solid state.

No change of crystalline form has been observed by XRPD for crystalline Forma A and crystalline form $H_A$. Therefore, Crystalline Forms A and $H_A$ were shown to have good physical stability properties.

Behavior under granulation simulation experiment: The physical stability of crystalline forms A and $H_A$ were also evaluated in granulation simulation experiments. In these experiments granulating solvent was added dropwise to the crystalline form A or $H_A$ until the solid is wetted sufficiently. The mixture was then vortexed between each addition at 25° C. Alternatively, dry grinding was carried out. The crystallinity of the material (post-grinding) was re-evaluated by XRPD and/or DSC. Under the dry grinding conditions, no form change was detected after grinding crystalline form $H_A$. Upon granulation using ethanol and water as the granulation solvent, XRPD results also indicated no form change.

Modification A was also stable under dry grinding conditions, however partially changed during granulation with water into crystalline form $H_A$.

Solubility

Form A is highly soluble at pH values of 4.7 and below (solubility higher than 2 mg/mL), however, at higher pH levels, formation of less soluble form $H_A$ leads to lower solubility values.

Form $H_A$ shows solubility in aqueous buffers in biorelevant media, of about 0.004 mg/mL.

In conclusion, crystalline form $H_A$ has shown chemical and physical stability in both solution and solid states but display lower solubility. Crystalline form $H_A$ is stable over a large humidity range and is highly crystalline. Crystalline form A is highly crystalline and anhydrous form. It has shown chemical and physical stability in solid state but converts to form $H_4$ in solvent with low water content. Form A is more soluble.

Definition

As used herein, the terms "about" and "substantially" indicate with respect to features such as endotherms, endothermic peak, exotherms, baseline shifts, etc., that their values can vary. With reference to X-ray diffraction peak positions, "about" or "substantially" means that typical peak position and intensity variability are taken into account. For example, one skilled in the art will appreciate that the peak positions (2θ) will show some inter-apparatus variability, typically as much as 0.2°. Occasionally, the variability could be higher than 0.2° depending on apparatus calibration differences. Further, one skilled in the art will appreciate that relative peak intensities will show inter-apparatus variability as well as variability due to degree of crystallinity, preferred orientation, prepared sample surface, and other factors known to those skilled in the art, and should be taken as qualitative measure only. For DSC, variation in the temperatures observed will depend upon the rate of temperature change as well as sample preparation technique and the particular instrument employed. Thus, the endotherm/melting point values reported herein relating to DSC/TGA thermograms can vary ±2° C. (and still be considered to be characteristic of the particular crystalline form described herein). When used in the context of other features, such as, for example, percent by weight (% by weight) the term "about" indicates a variance of ±3%.

As used herein "polymorph" refers to crystalline forms having the same chemical composition but different spatial arrangements of the molecules, atoms, and/or ions forming the crystal.

As used herein "amorphous" refers to a solid form of a molecule, atom, and/or ions that is not crystalline. An amorphous solid does not display a definitive X-ray diffraction pattern.

As used herein, "substantially phase pure," when used in reference to any crystalline form of the compound of Formula I, means a compound having a phase purity of greater than about 90% by weight, including greater than about 90, 91, 92, 93, 94, 95, 96, 97, 98, and about 99% by weight, and also including equal to about 100% by weight of the compound of Formula I, based on the weight of the compound on an anhydrous basis. The term "phase pure" or "phase purity" herein refers to phase homogeneity with respect to a particular solid state form of the compound of Formula I and does not necessarily imply a high degree of chemical purity absent an express statement to that effect. Phase purity may be determined according to methods known in the art, for example, using XRPD to do quantitative phase analysis using one or more approaches known in the art, for example, via an external standard method, direct comparisons of line (peak) characteristics which are attributed to different phases in a particular spectra, or via an internal standard method. However XRPD quantification of phase purity can be complicated by the presence of amorphous material. Accordingly, other methods that may be useful for determining phase purity include, for example, solid state NMR spectroscopy, Raman and/or infrared spectroscopy. One of skilled in the art would readily understand these methods and how to employ these additional (or alternative) methods for determining phase purity.

As used herein, "substantially chemically pure" when used in reference to any crystalline form of the compound of Formula I, means a compound having a chemical purity greater than about 90% by weight, including greater than about 90, 91, 92, 93, 94, 95, 96, 97, 98, and about 99% by weight, and also including equal to about 100% by weight of the compound of Formula I, based on the weight of the salt (on an anhydrous basis). The remaining material generally comprises other compounds, such as for example, other stereoisomers of the compound of Formula I, reaction impurities, starting materials, reagents, side products, and/or other processing impurities arising from the preparation and/or isolation and/or purification of the particular crystalline form. For example, a crystalline form of the compound of Formula I may be deemed to be substantially chemically pure if it has been determined to have a chemical purity of greater than about 90% by weight, as measured by standard and generally accepted methods known in the art, where the remaining less than about 10% by weight constitutes other materials such as other stereoisomers of the compound of Formula I, reaction impurities, starting materials, reagents, side products, and/or processing impurities. Chemical purity may be determined according to methods known in the art, for example, high performance liquid chromatography (HPLC), LC-MS (liquid chromatography—mass spectrometry), nuclear magnetic resonance (NMR) spectroscopy, or infrared spectroscopy. One of skill in the art would readily understand these methods and how to employ these additional (or alternative) methods for determining chemical purity.

The term "a therapeutically effective amount" of a compound of the present invention refers to an amount of the compound of the present invention that will elicit a biological or medical response in a subject, for example, reduction or inhibition of an enzyme or a protein activity, or ameliorate symptoms, alleviate conditions, or slow or delay disease progression, etc. In one non-limiting embodiment, the term "a therapeutically effective amount" refers to the amount of the compound of the present invention that, when administered to a subject, is effective to (1) at least partially alleviating, inhibiting, and/or ameliorating a condition, or a disorder or a disease (i) associated with the activity of TLR7 and/or TLR8, or (ii) characterized by activity (normal or abnormal) of TLR7 and/or TLR8 receptors; or (2) reducing or inhibiting the activity of TLR7 and/or TLR8 receptors. In another non-limiting embodiment, the term "a therapeutically effective amount" refers to the amount of the compound of the present invention that, when administered to a cell, or a tissue, or a non-cellular biological material, or a medium, is effective to at least partially reducing or inhibiting the activity of TLR7 and/or TLR8; or at least partially reducing or inhibiting the expression of TLR7 and/or TLR8 receptors.

As used herein, the term "subject" refers to an animal. Preferably, the animal is a mammal. A subject refers to for example, primates (e.g. humans), cows, sheep, goats, horses, dogs, cats, rabbits, rats, mice, fish, birds and the like. In a preferred embodiment, the subject is a human.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

As used herein, the term "inhibit", "inhibition" or "inhibiting" refers to the reduction or suppression of a given condition, symptom, or disorder, or disease, or a significant decrease in the baseline activity of a biological activity or process.

As used herein, the terms "treat," "treating," or "treatment" of any disease or disorder refers in one embodiment, to ameliorating the disease or disorder (i.e., slowing or arresting or reducing the development of the disease or at least one of the clinical symptoms thereof). In another embodiment, "treat," "treating," or "treatment" refers to alleviating or ameliorating at least one physical parameter including those which may not be discernible by the patient. In yet another embodiment, "treat," "treating," or "treatment" refers to modulating the disease or disorder, either physically, (e.g., stabilization of a discernible symptom), physiologically, (e.g., stabilization of a physical parameter), or both. In one embodiment, "treat" or "treating" refers to delaying the progression of the disease or disorder.

As used herein, the term "prevent", "preventing" or "prevention" of any disease or disorder refers to the prophylactic treatment of the disease or disorder; or delaying the onset of the disease or disorder.

The term "autoimmune disease," or "autoimmune disorder," as used herein, refers diseases wherein cells uncontrollably attack the body's own tissues and organs (autoimmunity), producing inflammatory reactions and other serious symptoms and diseases. Non-limiting examples of autoimmune diseases include idiopathic thrombocytopenic purpura, hemolytic anemia, systemic lupus erythematosus, cutaneous lupus, discoid lupus, rheumatoid arthritis (RA), multiple sclerosis (MS), systemic sclerosis, immune-mediated or type 1 diabetes mellitus, immune mediated glomerulonephritis, scleroderma, pernicious anemia, alopecia, pemphigus, pemphigus vulgaris, myasthenia gravis, inflammatory bowel diseases, Crohn's disease, Graves' disease, psoriasis, autoimmune thyroid diseases, Hashimoto's disease, Hashimoto's thyroiditis, polymyositis, dermatomyositis, CREST syndrome, Goodpasture's syndrome, mixed connective tissue disease myasthenia gravis pseudoparalytica, ophtalmia sympatica, phakogene uveitis, chronical aggressive hepatitis, primary billiary cirrhosis, autoimmune hemolytic anemy, Werlof disease, vitiligo vulgaris, Behcet's disease, collagen disease, uveitis, Sjögren's syndrome, autoimmune myocarditis, autoimmune hepatic diseases, autoimmune gastritis, pemphigus, Guillain-Barre syndrome, atherosclerosis, inflammatory bowel disease, ankylosing spondylitis, idiopathic thrombocytopenia, polyarteritis nodosa, primary biliary sclerosis, sarcoidosis, sclerosing cholangitis, Takayasu's arteritis, temporal arteritis, Wegener's granulomatosis and HTLV-1-associated myelopathy.

As used herein the term "combination" refers to either a fixed combination in one dosage unit form, or a combined administration where a crystalline form of compound of Formula I and a combination partner (i.e. an immunotherapeutic agent) may be administered independently at the same time or separately within time intervals, especially where these time intervals allow that the combination partners show a cooperative, e.g. synergistic effect. The single components may be packaged in a kit or separately. One or both of the components (e.g., powders or liquids) may be reconstituted or diluted to a desired dose prior to administration.

The terms "co-administration" or "combined administration" or the like as utilized herein are meant to encompass administration of the selected combination partner to a single subject in need thereof (e.g. a patient), and are intended to include treatment regimens in which the agents are not necessarily administered by the same route of administration or at the same time.

The term "pharmaceutical combination" and "combination product" are used interchangeably and refers to either a fixed combination in one dosage unit form, or non-fixed combination or a kit of parts for the combined administration where two or more therapeutic agents may be administered independently at the same time or separately within time intervals, especially where these time intervals allow that the combination partners show a cooperative, e.g. synergistic effect. The term "fixed combination" means that a crystalline form of the compound of Formula I and a combination partner (i.e. immunotherapeutic agent), are both administered to a patient simultaneously in the form of a single entity or dosage. The term "non-fixed combination" means that a crystalline form of the compound of Formula I and a combination partner (i.e. the immunotherapeutic agent), are both administered to a patient as separate entities either simultaneously, concurrently or sequentially with no specific time limits, wherein such administration provides therapeutically effective levels of the two compounds in the body of the patient. The latter also applies to cocktail therapy, e.g. the administration of three or more therapeutic agent. In a preferred embodiment, the pharmaceutical combination is a non-fixed combination.

The term "combination therapy" refers to the administration of two or more therapeutic agents to treat an autoimmune disorder as described in the present disclosure. Such administration encompasses co-administration of these therapeutic agents in a substantially simultaneous manner, such as in a single capsule having a fixed ratio of active ingredients. Alternatively, such administration encompasses co-administration in multiple, or in separate containers (e.g., tablets, capsules, powders, and liquids) for each active ingredient. Powders and/or liquids may be reconstituted or diluted to a desired dose prior to administration. In addition, such administration also encompasses use of each type of therapeutic agent in a sequential manner, either at approximately the same time or at different times. In either case, the treatment regimen will provide beneficial effects of the drug combination in treating the conditions or disorders described herein.

Pharmaceutical Composition, Combination, Dosage and Administration

In some embodiments the crystalline forms of (S)—N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)morpholine-3-carboxamide described herein can be used alone or they can be formulated into a pharmaceutical composition that also contains at least one pharmaceutically acceptable excipient, and often contains at least two or more pharmaceutically acceptable excipients. Some suitable excipients are disclosed herein. Other excipients may be used that are known in the art without departing from the intent and scope of the present application.

In some embodiments, the present invention utilizes a pharmaceutical composition comprising a compound of the present invention and a pharmaceutically acceptable excipient. The pharmaceutical composition can be formulated for particular routes of administration such as oral administration, parenteral administration, and rectal administration, etc. In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, carriers or buffering agents, as well as adjuvants, such as solvents, preservatives, stabilizers, wetting agents, emulsifiers and bulking agents, etc.

Typically, the pharmaceutical compositions are tablets or capsules comprising the active ingredient together with at least one excipient, such as:
 a) diluents, e.g., lactose, dextrose, sucrose, mannitol, sorbitol, cellulose and/or glycine;
 b) lubricants, e.g., silica, talcum, stearic acid, its magnesium or calcium salt and/or polyethyleneglycol; for tablets also
 c) binders, e.g., magnesium aluminum silicate, starch paste, gelatin, tragacanth, methylcellulose, sodium carboxymethylcellulose and/or polyvinylpyrrolidone; if desired;
 d) carriers such as an aqueous vehicle containing a co-solvating material such as captisol, PEG, glycerin, cyclodextrin, or the like;
 e) disintegrants, e.g., starches, agar, alginic acid or its sodium salt, or effervescent mixtures; and/or
 f) absorbents, colorants, flavors and sweeteners.

Tablets may be either film coated or enteric coated according to methods known in the art.

Preferably, the compound or composition is prepared for oral administration, such as a tablet or capsule, for example, and optionally packaged in a multi-dose format suitable for storing and/or dispensing unit doses of a pharmaceutical product. Examples of suitable packaging include, but are not limited to, hermetically sealed foils, unit dose containers (e. g., vials), blister packs, and strip packs.

Tablets may contain the active ingredient in admixture with nontoxic, pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

The present invention further provides anhydrous pharmaceutical compositions and dosage forms comprising the compounds of the present invention as active ingredients, since water may facilitate the degradation of certain compounds.

Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e. g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

The pharmaceutical composition or combination of the present invention can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., preferably aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.1-500 mg/kg, or between about 1-100 mg/kg.

In other embodiments, a pharmaceutical composition is provided which comprises at least one compound according to the embodiments supra and at least one carrier.

The crystalline forms of (S)—N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)morpholine-3-carboxamide as described herein are also useful as active pharmaceutical ingredients (APIs) as well as materials for preparing formulations that incorporate one or more pharmaceutically acceptable excipients and are suitable for administration to human subjects.

As used herein, the term "pharmaceutically acceptable excipients" includes any and all solvents, carriers, diluents, dispersion media, coatings, surfactants, antioxidants, preservatives (e.g., antibacterial agents, antifungal agents, antioxidants), isotonic agents, absorption delaying agents, salts, drug stabilizers, binders, additives, bulking agents, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). It should be understood that unless a conventional excipient is incompatible with the active ingredient, the use of any conventional excipient in any therapeutic or pharmaceutical compositions is contemplated by the present application.

Accordingly, in an embodiment of the disclosure, a crystalline form of (S)—N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)morpholine-3-carboxamide (Form A or Form $H_A$) is provided in a substantially phase pure form. This crystalline form of a (S)—N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)morpholine-3-carboxamide (Form A or Form $H_A$) in substantially phase pure form may be used to prepare pharmaceutical compositions which may further comprising one or more pharmaceutically acceptable excipients. In some embodiments the crystalline form of (S)—N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)morpholine-3-carboxamide may not retain its crystallinity in the pharmaceutical composition. For example, in some embodiments crystalline Form A or $H_A$ may be used in a process to prepare a pharmaceutical composition that, for example, involves spray drying or wet granulation; thus it could be that little to no crystalline Form A or $H_A$ is detected in the resulting pharmaceutical composition.

Therapeutic Kits

In one embodiment, the invention provides a kit comprising two or more separate pharmaceutical compositions, at least one of which contains a crystalline form of the compound of formula (I) (Form A or Form $H_A$). In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, a crystalline form of a compound of Formula (I) (i.e. Form A or Form $H_A$) and the other therapeutic agent may be manufactured and/or formulated by the same or different manufacturers. Moreover, a crystalline form of the compound of Formula (I) and the other therapeutic may be brought together into a combination therapy: (i) prior to release of the combination product to physicians (e.g. in the case of a kit comprising a crystalline form of compound of Formula (I) and the other therapeutic agent); (ii) by the physician themselves (or under the guidance of the physician) shortly before administration; (iii) in the patient themselves, e.g. during sequential administration of a crystalline form of the compound of Formula (I) and the other therapeutic agent.

Accordingly, the invention provides the use of a crystalline form as described herein (i.e. Form A or Form $H_A$), for treating autoimmune diseases, wherein the medicament is prepared for administration with another therapeutic agent. The invention also provides the use of an therapeutic agent for treating autoimmune diseases, wherein the medicament is administered with a crystalline form of the compound of Formula (I).

The invention also provides a crystalline form of the compound of Formula (I) (i.e. Form A or Form $H_A$), for use in a method of treating autoimmune diseases, wherein the crystalline form of compound of Formula (I) is prepared for administration with another therapeutic agent. The invention also provides another immunotherapeutic agent for use in a method of treating autoimmune diseases, wherein the other therapeutic agent is prepared for administration with a crystalline form of compound of Formula (I). The invention also provides crystalline form of compound of Formula (I), for use in a method of treating autoimmune diseases, wherein the crystalline form of compound of Formula (I) is administered with another therapeutic agent. The invention also provides another therapeutic agent for use in a method of treating autoimmune diseases, wherein the other therapeutic agent is administered with a crystalline form of compound of Formula (I).

The invention also provides the use of a crystalline form of compound of Formula (I), for treating autoimmune diseases, wherein the patient has previously (e.g. within 24 hours) been treated with another therapeutic agent. The invention also provides the use of another therapeutic agent for treating autoimmune diseases, wherein the patient has previously (e.g. within 24 hours) been treated with a crystalline form of compound of Formula (I).

Combination:

The additional therapeutic agents used in combination with a crystalline form of the invention, include, but are not limited to anti-inflammatory agents, immunomodulatory agents, immunosuppressive agents, cytokines, nonsteroidal anti-inflammatory drugs (NSAIDs), antimalarial compounds, anti-rheumatic compounds, inhibitors of B-cell activating factor (BAFF), inhibitors of B-lymphocyte stimulator (BLyS), and steroid hormones.

Nonsteroidal anti-inflammatory drugs (NSAIDs) used in combination with compounds of the invention, include, but are not limited to, salicylic acid, acetylsalicylic acid, methyl salicylate, diflunisal, salsalate, olsalazine, sulfasalazine, acetaminophen, indomethacin, sulindac, etodolac, mefenamic acid, meclofenamate sodium, tolmetin, ketorolac, dichlofenac, ibuprofen, naproxen, naproxen sodium, fenoprofen, ketoprofen, flurbinprofen, oxaprozin, piroxicam, meloxicam, ampiroxicam, droxicam, pivoxicam, tenoxicam, nabumetome, phenylbutazone, oxyphenbutazone, antipyrine, aminopyrine, apazone and nimesulide.

Anti-rheumatic compound used in combination with compounds of the invention, include, but are not limited to, methotrexate.

Antimalarial compound used in combination with compounds of the invention, include, but are not limited to, chloroquine and hydroxycloroquine.

Inhibitors of B-cell activating factor (BAFF), also known as inhibitors of B-lymphocyte stimulator (BLyS), used in combination with compounds of the invention, include, but are not limited to, belimumab (Benlysta®), Blisibimod and BR3-Fc.

Immunosuppressive agents used in combination with compounds of the invention, include, but are not limited to, mycophenolate mofetil (MMF), mycophenolic acid, cyclophosphamide, azathioprine and Laquinimod (5-chloro-N-ethyl-4-hydroxy-1-methyl-2-oxo-N-phenyl-1,2-dihydroquinoline-3-carboxamide).

Steroid hormones used in combination with compounds of the invention, include, but are not limited to, dehydroepiandrosterone (DHEA).

Preparation of crystalline form of (S)—N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl) morpholine-3-carboxamide Crystalline forms may be prepared by a variety of methods, including for example, crystallization or recrystallization from a suitable solvent, sublimation, growth from a melt, solid state transformation from another phase, crystallization from a supercritical fluid, and jet spraying. Techniques for crystallization or recrystallization of crystalline forms from a solvent mixture include, for example, evaporation of the solvent, decreasing the temperature of the solvent mixture, crystal seeding a supersaturated solvent mixture of the molecule and/or salt, freeze drying the solvent mixture, and addition of antisolvents (countersolvents) to the solvent mixture. Exemplary methods of preparing the crystalline forms described herein are set forth in detail below.

Crystals of drugs, including polymorphs, methods of preparation, and characterization of drug crystals are discussed in *Solid-State Chemistry of Drugs*, S. R. Byrn, R. R. Pfeiffer, and J. G. Stowell, $2^{nd}$ Edition, SSCI, West Lafayette, Indiana (1999).

For crystallization techniques that employ solvents, the choice of solvent or solvents is typically dependent upon one or more factors, such as solubility of the compound, crystallization technique, and vapor pressure of the solvent. Combinations of solvents may be employed, for example, the compound may be solubilized into a first solvent to afford a solution, followed by the addition of an antisolvent to decrease the solubility of the compound in the solution and to afford the formation of crystals. An antisolvent is a solvent in which the compound has low solubility.

In one method to prepare crystals, a compound is suspended and/or stirred in a suitable solvent to afford a slurry, which may be heated to promote dissolution. The term "slurry", as used herein, means a saturated solution of the compound, which may also contain an additional amount of the compound to afford a heterogeneous mixture of the compound and a solvent at a given temperature. This may also be referred to as a suspension.

Seed crystals may be added to any crystallization mixture to promote crystallization. Seeding may be employed to control growth of a particular polymorph or to control the particle size distribution of the crystalline product. Accordingly, calculation of the amount of seeds needed depends on the size of the seed available and the desired size of an average product particle as described, for example, in "Programmed Cooling of Batch Crystallizers," J. W. Mullin and J. Nyvlt, *Chemical Engineering Science,* 1971,26, 369-377. In general, seeds of small size are needed to control effectively the growth of crystals in the batch. Seed of small size may be generated by sieving, milling, or micronizing of large crystals, or by micro-crystallization of solutions. Care should be taken that milling or micronizing of crystals does not result in any change in crystallinity form the desired crystal form (i.e., change to amorphous or to another polymorph).

A cooled crystallization mixture may be filtered under vacuum, and the isolated solids may be washed with a suitable solvent, such as cold recrystallization solvent, and dried under a nitrogen purge to afford the desired crystalline form. The isolated solids may be analyzed by a suitable spectroscopic or analytical technique, such as solid state nuclear magnetic resonance, differential scanning calorimetry, x-ray powder diffraction, or the like, to assure formation of the preferred crystalline form of the product. The resulting crystalline form is typically produced in an amount of greater than about 70 weight % isolated yield, preferably greater than 90 weight % isolated yield, based on the weight of the compound originally employed in the crystallization procedure. The product may be co-milled or passed through a mesh screen to delump the product, if necessary.

Alternatively, crystalline forms may be prepared directly from the reaction medium of the final process for preparing (S)—N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)morpholine-3-carboxamide. This may be achieved, for example, by employing in the final process step a solvent or a mixture of solvents from which (S)—N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)morpholine-3-carboxamide may be crystallized. In addition, crystalline forms may be obtained by distillation or solvent addition techniques.

In addition to the methods discussed briefly below, it should be understood that various analytical methods may be used for the characterization of any of the materials described herein.

The following non-limiting examples are illustrative of the disclosure.

EXAMPLES

Abbreviation

DIPEA: N,N-diisopropylethylamine
HATU: 0-(7-azobenzotriazol-1-yl)-1,1,3,3-tetramethyluoniumhexafluorophosphate
DCM: dichloromethane
THF: tetrahydrofuran Example 1: Preparation of the Crystalline Form A

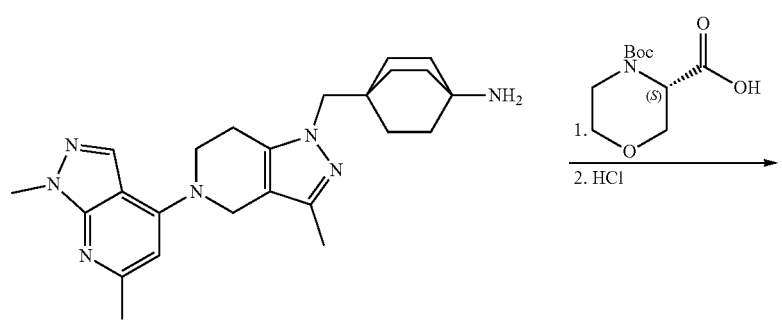

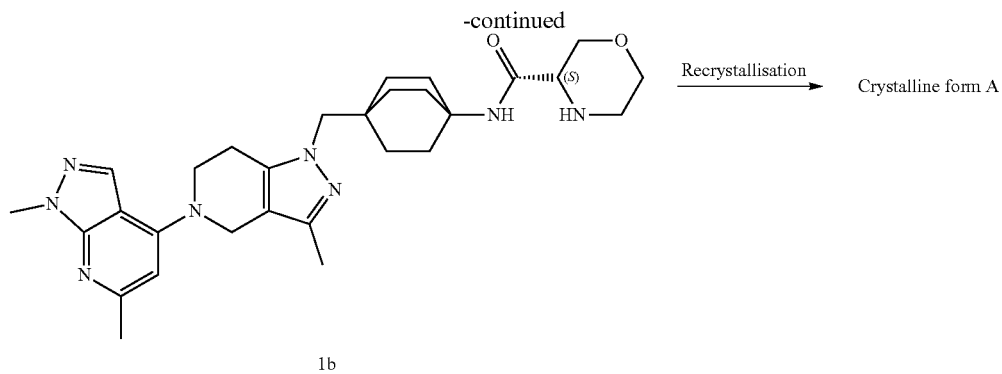

1b (S)-4-(tert-butoxycarbonyl)morpholine-3-carboxylic acid (637 g, 2.75 mol) was dissolved in THF (1.1 L), DIPEA (508 g, 3.9 mol), HATU (1097 g, 2.9 mol) and 4-((5-(1,6-dimethyl-1H-pyrazolo[3,4-b]pyridine-4-yl)-3-methyl-4,5,6,7-tetrahydro-1H-pyrazolo[4,3-c]pyridin-1yl)methyl)bicyclo[2.2.2]octan-1-amine (1a, 1.1 kg, 2.6 mol as described in WO2018/047081) were added, the mixture was stirred from a yellow suspension to a yellow solution for 16 h, HPLC indicated the reaction was finished, The mixture was quenched with water (7.4 kg), extracted with DCM (14.6 kg), The DCM layer was washed with 0.5 M HCl solution (5.5 kg, to remove DIPEA completely) and sat. NaCl solution (5.5 kg), the DCM layer was separated.

To this DCM layer was added water (5.3 kg) and 31% HCl solution (1.2 kg). The mixture was stirred at 35° C. for 16 h, HPLC indicated the deprotection reaction was finished. The reaction mixture was cooled to room temperature, separated and the organic layer was discarded. To the water phase was added DCM (14.6 kg), and 20% NaOH solution (~3.2 kg) was added under stirring to a pH >8. The organic layer was separated and washed with 5% NaOH (5.5 kg*2, to remove the $HPF_6$ completely), then washed with water (5.5 kg*3), the organic layer was dried with $Mg_2SO_4$ and filtered, then concentrated under reduced pressure to yield (S)—N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)morpholine-3-carboxamide as a free base (1b).

Recrystallization Step:

The material obtained above (1b) was taken up in acetone (8.7 kg*3), and warmed up to an internal temperature of 50° C., then was cooled down to 15° C. over a period of 4 h. The heating/cooling cycle was repeated twice to form a white suspension. The white suspension was heated to 50° C., heptane (15.6 kg) was added drop wise, the suspension was stirred at an internal temperature of 50° C. for 1 h, then cooled to an internal temperature of 15° C. over a period of 4 h. The mixture was stirred at 15° C. for 1 h, filtered, washed with acetone/heptane (0.87 kg/1.56 kg), and dried at 50° C. for 16 h to give a white solid 890 g. The white solid was analyzed by XRPD, DSC and TGA (FIGS. 1-3 respectively).

Example 2: Preparation of the Hydrate Crystalline Form $H_A$

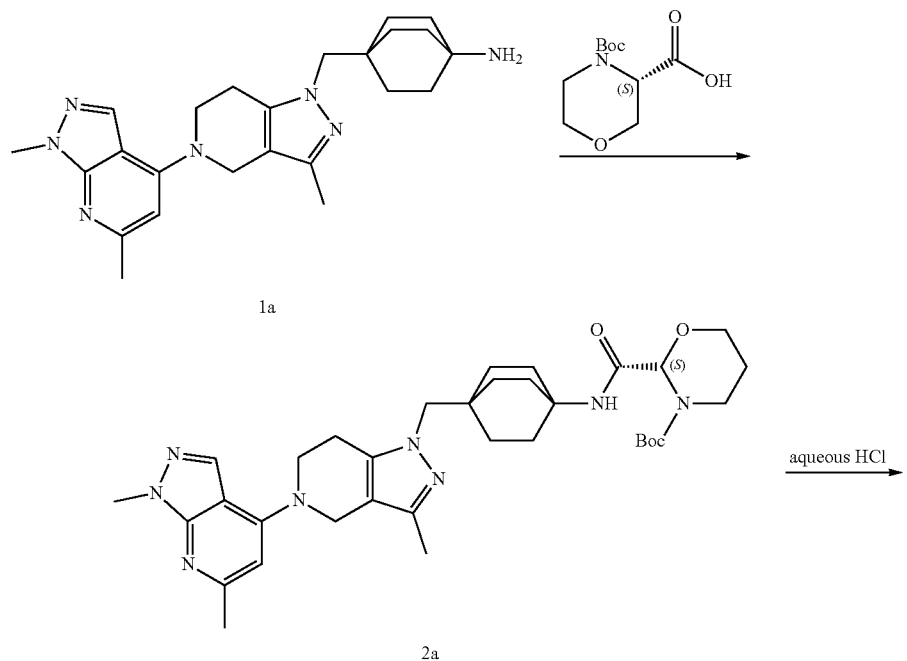

1a

2a

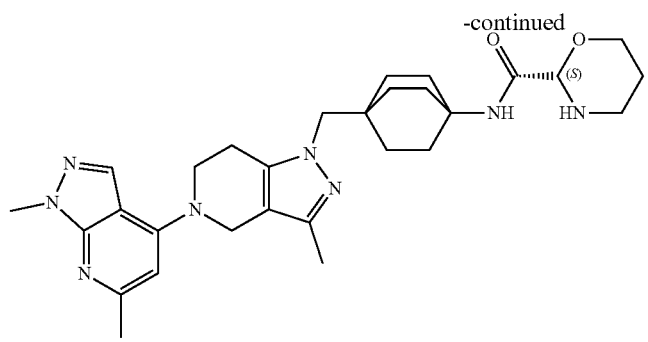

2b

A mixture of (3S)-4-(tert-Butoxycarbonyl)morpholine-3-carboxylic acid (6.06 g, 26.2 mmol) and 4-methylmorpholine (3.62 g, 35.8 mmol) in 125 ml of dichloromethane is added 4-{[5-(1,6-Dimethyl-1H-pyrazolo[3,4-b]pyridin-4-yl)-3-methyl-4,5,6,7-tetrahydro-1H-pyrazolo[4,3-c]pyridin-1-yl]methyl}bicyclo[2.2.2]octan-1-amine (1a, 10.0 g, 23.8 mmol, as described in WO2018/047081) in 25 ml of dichloromethane, HATU (10.9 g, 28.6 mmol) is added then the mixture is stirred at room temperature for 16 hours. After completion of the conversion, the reaction mixture is washed with aqueous sodium hydroxide solution and aqueous sodium chloride solution. The separated organic layer is concentrated and treated with hydrochloride 2-propanol solution in tert-butyl methyl ether. The resulted suspension is filtered and washed by tert-butyl methyl ether and the product tert-Butyl (3S)-3-[(4-{[5-(1,6-dimethyl-1H-pyrrolo[2,3-b]pyridin-4-yl)-3-methyl-4,5,6,7-tetrahydro-1H-pyrazolo[4,3-c]pyridin-1-yl]methyl}bicyclo[2.2.2]octan-1-yl)carbamoyl]morpholine-4-carboxylate (2a) is isolated and dried as a hydrochloric salt.

To a mixture of product tert-Butyl (3S)-3-[(4-{[5-(1,6-dimethyl-1H-pyrrolo[2,3-b]pyridin-4-yl)-3-methyl-4,5,6,7-tetrahydro-1H-pyrazolo[4,3-c]pyridin-1-yl]methyl}bicyclo[2.2.2]octan-1-yl)carbamoyl]morpholine-4-carboxylate (2a, 7.56 g, 11.3 mmol) in 70 ml of water is added 50 ml of dichloromethane, 31% aqueous hydrochloride solution (4.65 g, 39.5 mmol) then is added and the mixture is stirred at 372c for 16 hours. After completion of the conversion, dichloromethane phase is separated and the aqueous layer is washed with tert-butyl methyl ether. The pH value of the aqueous phase is adjusted to 7-8 with 16% aqueous sodium hydroxide solution, 25 ml of 2-propanol was added and pH value is further adjusted to 8-9 with 16% aqueous sodium hydroxide solution. The pH of the mixture is further adjusted to >12 with 16% aqueous sodium hydroxide solution. The resulted suspension is filtered and slurred in 2-propanol/Water (70 ml/5 ml), the solid is collected by filtration and washed by water/2-propanol (50 ml/3 ml), and the product (S)—N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)morpholine-3-carboxamide(2b) is isolated and dried as a free form.

Recrystallization Step:

(S)—N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)morpholine-3-carboxamide (2b) described above) is suspended in a mixture of Acetone/water 98:2 (w:w) and heated to 50° C. to dissolve everything. After clear filtration water is added to the solution to have a 95:5 Acetone/water (w:w) mixture.

Solution is seeded at 45° C. The suspension is then cooled down to −10° C. The product is isolated and washed with a mixture of Acetone/Water 95:5 (w:w), filtrated and gently dried under vacuum.

The drying can also be performed in the presence of water.

Alternatively, (S)—N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)morpholine-3-carboxamide (2b as described above) is suspended in Isopropanol 95:5 water (w:w) and heated to 50° C. to dissolve everything. After clear filtration the solution is cooled to 25° C. and seeded. More water is added and cooled to −10° C. The product is isolated and gently dried under vacuum.

The drying can also be performed in the presence of water.

Other solvents which can be used in the process described above, resulting in the formation of the hydrate crystalline form $H_A$ (always in combination with water) are other alcohols such as ethanol, methanol and isobutanol; THF or acetonitrile.

Powder X-Ray Diffraction

X-ray powder diffraction (XRPD) data were obtained using a Bruker Discovery D8 with a LynxEye detector. Powder samples were placed on a zero-background Si-sample holder. The radiation was Cu Kα (1=1.5418 Å). Data were collected between 2-40° 2theta with a sample exposure time of at least 300 seconds.

TABLE 1

X-ray powder diffraction data for crystalline form A

| Angle °2theta | d value Angstrom | Intensity % |
|---|---|---|
| 4.06 | 21.744 | 38 |
| 8.17 | 10.810 | 9 |
| 15.20 | 5.823 | 15 |
| 16.33 | 5.424 | 48 |
| 16.92 | 5.235 | 16 |
| 18.20 | 4.871 | 27 |
| 18.67 | 4.750 | 100 |
| 19.82 | 4.477 | 29 |
| 20.46 | 4.338 | 18 |
| 21.61 | 4.108 | 25 |
| 23.08 | 3.851 | 10 |
| 24.60 | 3.616 | 14 |
| 24.43 | 3.641 | 14 |
| 26.22 | 3.397 | 14 |

TABLE 2

X-ray powder diffraction data for crystalline hydrate form $H_A$

| Angle °2theta | d value Angstrom | Intensity % |
|---|---|---|
| 6.59 | 13.412 | 14 |
| 7.12 | 12.404 | 3 |
| 10.61 | 8.330 | 6 |
| 13.24 | 6.682 | 6 |
| 14.28 | 6.196 | 100 |
| 14.87 | 5.953 | 14 |
| 15.63 | 5.666 | 8 |
| 15.99 | 5.539 | 23 |
| 17.36 | 5.105 | 21 |
| 18.55 | 4.781 | 7 |
| 18.87 | 4.700 | 15 |
| 21.46 | 4.138 | 14 |
| 22.23 | 3.996 | 10 |
| 22.84 | 3.890 | 10 |
| 23.53 | 3.778 | 10 |
| 25.30 | 3.517 | 7 |
| 26.47 | 3.365 | 8 |
| 27.36 | 3.257 | 8 |

Thermal Analysis (TA):

The crystalline forms were analyzed using a TA instrument Discovery (DSC) and thermogravimetric analysis (TGA): Discovery (DSC) and Discovery (TGA) with aluminum pans (T150603); heating rate 10° C./min, temperature range: 30 to 300° C.

DSC:

Differential scanning calorimetry was conducted for each crystalline form using a TA Instruments, model Discovery. For each analysis, the DSC cell is purged with 50 ml/min of ultra-high purity nitrogen gas. The instrument was calibrated with high purity indium. The heating rate was 10° C. per minute in the temperature range between 30 and 300° C. The heat flow, which is normalized by sample weight, is plotted versus the measured sample temperature. Temperatures are reported in degrees Celsius (° C.) and enthalpies are reported in Joules per gram (J/g). Plots are showing endothermic peaks as down. The endothermic melt peak (melting point) was evaluated for extrapolated onset temperature. The accuracy of the measured sample temperature with this method is within about 1° C., and the heat of fusion can be measured within a relative error of about ±5%.

Illustrative DSC traces generated using crystalline Forms A and $H_A$ are shown in FIGS. 2 and 4, respectively.

Form A: Melting endotherm: $T_{onset}$=182.7° C., ΔH=65 J/g

Form $H_A$: Melting endotherm: $T_{onset}$=54.2° C. with an enthalpy ΔH of 284 J/g and $T_{onset}$=130.6° C. with an enthalpy ΔH of 24 J/g

TGA:

The TGA instruments used to test the crystalline forms was a Q5000 TA Instruments model. Samples of 10 to 20 milligrams were analyzed at a heating rate of 10° C./min in the temperature range between 25° C. to 300° C. under a constant flow of 20 ml/min of ultra-high purity nitrogen gas. The weight loss is plotted against the measured sample temperature. Temperatures are reported in degrees Celsius (° C.) and weight loss in %.

Illustrative TGA traces generated using crystalline Forms A and $H_A$ are shown in FIGS. 3 and 6, respectively.

What is claimed is:

1. A crystalline form of the compound (S)—N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)morpholine-3-carboxamide in its free form, wherein the compound is a hydrate, and the crystalline form is characterized by one of the following characteristics:
   (i) an x-ray powder diffraction pattern comprising representative peaks in terms of 2θ at 6.6±0.2°2θ, 16.0±0.2°2θ, and 17.3±0.2°2θ, measured at a temperature of about 25° C. and an x-ray wavelength, λ, of 1.5418 Å;
   (ii) an x-ray powder diffraction pattern comprising four or more 2θ values selected from the group consisting of 6.6±0.2°, 71±0,20, 10.6±0.2°, 13.2±0.2°, 14.3±0.2, 16.0±0.2°, 17.3±0.2°, 23.5±0.2°, 26.5±0.2 and 27.3±0.2°2θ, measured at a temperature of about 25° C. and an x-ray wavelength, λ, of 1.5418 Å; and
   (iii) an x-ray powder diffraction pattern comprising five or more 2θ values selected from the group consisting of 6.6±0.2°, 7.1±0.20, 10.6±0.2°, 13.2±0.2°, 14.3±0.2°, 16.0±0.2°, 17.3±0.2°, 23.5±0.2°, 26.5±0.2 and 27.3±0.2°2θ, measured at a temperature of about 25° C. and an x-ray wavelength, λ, of 1.5418 Å.

2. The crystalline form according to claim 1 having a differential scanning calorimetry (DSC) thermogram that shows melting endotherms at $T_{onset}$=54.2° C. with an enthalpy ΔH of 284 J/g and at $T_{onset}$=130.6° C. with an enthalpy ΔH of 24 J/g when heated from 30 and 300° C. at a rate of 10° C. per minute.

3. The crystalline form according to claim 1 having a thermo gravimetric analysis (TGA) diagram that shows a weight loss of 9.9% at 96° C. when heated from 30 and 300° C. at a rate of 10° C. per minute.

4. The crystalline form according to claim 1, wherein the hydrate is a hemiheptahydrate.

5. The crystalline form according to claim 1, wherein crystalline form is in a substantially pure phase form.

6. A pharmaceutical composition comprising the crystalline form according to claim 1; and one or more pharmaceutically acceptable excipients.

7. The pharmaceutical composition according to claim 6 wherein the crystalline form is in a substantially pure phase form.

8. A pharmaceutical composition comprising the crystalline form according to claim 1; in combination with one or more therapeutic agents, wherein the therapeutic agent is independently selected from the group consisting of anti-inflammatory agents, immunomodulatory agents, immunosuppressive agents, cytokines, nonsteroidal anti-inflammatory drugs (NSAIDs), antimalarial compounds, antirheumatic compounds, inhibitors of B-cell activating factor (BAFF), inhibitors of B-lymphocyte stimulator (BLyS), and steroid hormones.

9. The pharmaceutical composition according to claim 8 wherein the crystalline form is in a substantially pure phase form.

10. A method of treating an autoimmune disease associated with the activity of an endosomal Toll-like Receptor selected from TLR7 and TLR8 in a subject in need thereof, comprising administering to the mammal a therapeutically-effective amount of the crystalline form according to claim 1, wherein the autoimmune disease associated with the activity of an endosomal Toll-like Receptor selected from TLR7 and TLR8 is selected from systemic lupus erythematosus, cutaneous lupus, mixed connective tissue disease, primary biliary cirrhosis, immune thrombocytopenia purpura, dermatornyositis, polymyositis, Sjögren's syndrome, arthritis, rheumatoid arthritis and psoriasis.

11. The method according to claim 10 wherein the crystalline form is in a substantially pure phase form.

12. The method according to claim 10, wherein the subject is a human.

13. A process for making the crystalline form of compound (S)—N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)morpholine-3-carboxamide according to claim 1, comprising the steps of:
  a) Suspending an amorphous free form of (S)—N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)morpholine-3-carboxamide in a solvent mixture containing at least about 2% by weight of water to form a suspension mixture,
  b) Heating the suspension mixture to a temperature until dissolution to form a solution,
  c) Cooling the solution to about −10° C. to form a suspension,
  d) Filtering the suspension to collect the crystalline form.

14. The process according to claim 13 wherein the solvent mixture in step a) comprises acetone, alcohol, tetrahydrofuran or acetonitrile.

15. The process according to claim 13 wherein the solvent mixture in step a) is selected from acetone/water 98:2 (weight by weight) and isopropanol/water 95:5 (weight by weight).

* * * * *